United States Patent
Ignatious et al.

(10) Patent No.: US 7,026,431 B2
(45) Date of Patent: Apr. 11, 2006

(54) SUSTAINED RELEASE IONIC CONJUGATE

(75) Inventors: Francis Xavier Ignatious, Millville, MA (US); Thomas Ciaran Loughman, Dublin (IE); Shalaby Wahba Shalaby, Pendleton, SC (US); Franck Jean-Claude Touraud, Vernon (FR)

(73) Assignee: Ipsen Manufacturing Ireland Limited, Dublin (IE)

( * ) Notice: Subject to any disclaimer, the term of this patent is extended or adjusted under 35 U.S.C. 154(b) by 86 days.

(21) Appl. No.: 10/636,357

(22) Filed: Aug. 7, 2003

(65) Prior Publication Data

US 2005/0074492 A1 Apr. 7, 2005

Related U.S. Application Data

(60) Division of application No. 09/171,740, filed on Apr. 20, 1999, which is a continuation of application No. PCT/IE97/00030, filed on Apr. 22, 1997, now Pat. No. 6,911,218.

(30) Foreign Application Priority Data

Apr. 23, 1996 (IE) ..................... 960308

(51) Int. Cl.
*C08G 63/02* (2006.01)
(52) U.S. Cl. ..................... 528/271; 528/272
(58) Field of Classification Search ............ 528/271, 528/272
See application file for complete search history.

(56) References Cited

U.S. PATENT DOCUMENTS

| | | |
|---|---|---|
| 3,773,919 A | 11/1973 | Boswell et al. |
| 4,767,628 A | 8/1988 | Hutchinson et al. |
| 5,084,553 A | 1/1992 | Hess et al. |
| 5,480,656 A | 1/1996 | Okada et al. |
| 5,643,607 A | 7/1997 | Okada et al. |
| 5,814,342 A | 9/1998 | Okada et al. |

FOREIGN PATENT DOCUMENTS

| | | | |
|---|---|---|---|
| CA | 2054397 | | 4/1992 |
| CA | 2144310 | | 3/1994 |
| CA | 2250981 | | 10/1997 |
| EP | 0 442 671 A2 | | 8/1991 |
| EP | 0 556 917 A1 | | 2/1993 |
| EP | 0442 671 B1 | | 6/1995 |
| GB | 2 277 915 A | | 5/1994 |
| HU | 211 586 A9 | | 6/1995 |
| JP | S59-33214 | | 8/1982 |
| JP | 2003183364 | * | 7/2003 |
| WO | WO93/17668 | | 9/1993 |
| WO | WO-94/15587 | | 7/1994 |

* cited by examiner

*Primary Examiner*—Carlos A. Azpuru
(74) *Attorney, Agent, or Firm*—Fish & Richardson; Brian R. Morrill; Alan F. Feeney

(57) ABSTRACT

A method of spherifying a sustained release ionic conjugate which contains a free carboxyl group-containing biodegradable polymer and a free amino group-containing drug which are ionically bonded to each other.

2 Claims, No Drawings

SUSTAINED RELEASE IONIC CONJUGATE

CROSS REFERENCE TO RELATED APPLICATIONS

This is a divisional of U.S. application Ser. No. 09/171,740, now U.S. Pat. No. 6,911,218 filed Apr. 20, 1999 which is a continuation of International Patent Application No. PCT/IE97/00030, with an international filing date of Apr. 22, 1997, which claims priority to Irish Patent Application No. 960308, filed Apr. 23, 1996.

TECHNICAL FIELD

This invention relates to sustained release drug delivery systems and, in particular, to a method of making microparticles of a sustained release ionic conjugate.

BACKGROUND ART

Biodegradable polymeric drug delivery formulations have been developed and utilized for the controlled in vivo release of drugs. See, e.g., U.S. Pat. Nos. 3,773,919 and 4,767,628. Such biodegradable polymeric formulations are designed to allow an entrapped drug to slowly diffuse through a polymer matrix or coating when the biodegradable polymer is depolymerized.

International Publication No. WO 94/15587 describes sustained release ionic molecular conjugates of polyesters and drugs. Since polyester degradation is a key step in the release process, the surface area of the conjugate particles can control the release profile of the drug from the conjugate. Thus, the conjugate particles should be of similar size and shape to insure both the minimum and reproducible surface area, e.g., microspheres.

DISCLOSURE OF INVENTION

In one aspect, this invention features a method of making microparticles of a sustained release ionic conjugate containing a free carboxyl group-containing biodegradable polymer (a polyester made of monomers such as lactic acid, e-caprolic acid, glycolic acid, trimethylene carbonate, or p-dioxanone; or a copolymer thereof, the monomers can be optically isomers or racemates) and a free amino group-containing drug (e.g., a peptide drug such as somatostatin or LHRH) which are ionically bonded to each other. The method includes the steps of (1) obtaining a first solution in which the conjugate is dissolved; (2) mixing the first solution (added as small droplets, e.g., through an atomizing nozzle such as sonic nozzle, pneumatic nozzle, rotary atomizer, or pressure nozzle) with a first liquid to form a first dispersion, wherein the first liquid is miscible with the first solution, and the conjugate is not soluble in the first liquid and precipitates out of the first dispersion; and (3) isolating the conjugate from the first dispersion.

In one embodiment, the drug is soluble in the first liquid, which can be an alcohol (e.g., ethanol or isopropyl alcohol), hexane, or water; or a mixture thereof. When ethanol is used as the first liquid, it can be maintained between about 0° C. and −30° C. when it is being used. When isopropyl alcohol is used, it can be maintained between about 0° C. and −70° C., e.g., cooled by the addition of dry ice.

The first solution, which may contain acetone, dichloromethane, acetonitrile, ethyl acetate, tetrahydrofuran, or glyme, or mixtures thereof can be obtained by (1) dissolving the biodegradable polymer in a second liquid (e.g., acetone, tetrahydrofuran, glycone, ethyl acetate, methyl acetate, acetonitrile, ethyl formate, or glyme; or a mixture thereof) to form a second solution; (2) dissolving the drug in a third liquid (e.g., water or acetone; or a mixture thereof) to form a third solution, wherein the third liquid is miscible with the first liquid and the second liquid; and (3) mixing the second solution and the third solution to form the first solution, wherein the mixing causes the drug to ionically bond to the biodegradable polymer and form the conjugate in the first solution. The first solution may comprise up to 40% by weight of the conjugate (e.g., between 25 and 35 percent by weight of the conjugate). In one example, a base, e.g., NaOH or KOH, can be added to the second solution prior to mixing the second solution and the third solution. Neutralization of the carboxyl groups of the biodegradable polymer with the base facilitates the formation of the ionic conjugate.

Alternatively, the first solution is obtained by dissolving the biodegradable polymer and the drug in a second liquid (e.g., acetone or a mixture of acetone and water) to form the first solution, thereby forming the conjugate in the first solution. According to this method, the biodegradable polymer can be first dissolved in the second liquid, a base is then added to the second solution, and the drug is subsequently dissolved in the second liquid. Also, if desired, the first solution can be partially or completely evaporated from the first dispersion prior to isolation of the conjugate. The processed conjugate can be conveniently isolated by centrifuging or filtering the first dispersion, and the isolated conjugate can be mixed with an aqueous mannitol solution prior to vacuum drying (e.g., lyophilization). The isolated conjugate can be further shaped into a film or a rod. The isolated conjugate can also be spherified into microspheres of average diameter of 5 to 200 μm, e.g., as described herein. By "spherification" or "spherifying" is meant the processing of a microparticle into a shape close to a sphere.

In another aspect, this invention features a method of spherifying a sustained release ionic conjugate as described above. The method includes the steps of (1) mixing the conjugate with a first liquid (e.g., an oil such as silicon oil, mineral oil, sesame oil, or a vegetable oil) to form a first dispersion, wherein the conjugate has the shape of a microparticle and is not soluble in the first liquid; (2) heating the first dispersion to a temperature greater than the Tg or Tm of the conjugate; (3) cooling the first dispersion below the Tg or Tm of the conjugate; (4) mixing the first dispersion with a second liquid (e.g., hexane, heptane, isopropyl myristate, or an alcohol such as ethanol or isopropyl alcohol) to form a second dispersion, wherein the second liquid is miscible with the first liquid and the conjugate is not soluble in the second liquid; and (5) isolating the conjugate from the second dispersion. The conjugate may have the shape of a microcapsule with an average diameter of between 5 μm to 200 μm prior to mixing with the first liquid, and the first dispersion thus formed is vigorously stirred while being heated to aid in the separation of the particles. Once the conjugate has been isolated, it can be rinsed with the second liquid and then vacuum dried. Optionally, it can also be mixed with an aqueous mannitol solution prior to vacuum drying.

A third aspect of this invention features a method of spherifying the above-described sustained release ionic conjugate (e.g., a microcapsule having an average diameter of between 5 μm to 200 μm). The method includes the steps of (1) mixing the conjugate in a first liquid (e.g., water) to form a first dispersion, wherein the conjugate is in the shape of a microparticle and the conjugate is not soluble in the first liquid; (2) stirring the first dispersion; (3) mixing the stirred dispersion with a second liquid (e.g., dichloromethane or chloroform) in such an amount so that it is absorbed by the conjugate but does not solubilize the conjugate, wherein the second liquid is miscible with the first liquid; (4) evaporating the second liquid from the first dispersion; and (5) isolating the precipitated conjugate from the first dispersion. If necessary, the method may further include the step of adding a surfactant (e.g., lecithin, Tween 20, polysorbate, or lauryl sulfate) to the first dispersion to aid in the stabilization of the first dispersion, and the isolated conjugate can be rinsed with the first liquid and vacuum dried. Again, the isolated conjugate can be mixed with an aqueous mannitol solution prior to vacuum drying.

In a further aspect of this invention, this invention features a method of spherifying the above-described sustained release ionic conjugate. The method includes the steps of (1) dissolving the conjugate in a first liquid (e.g., acetonitrile) to form a first solution; (2) stirring the first solution with a second liquid (e.g., an oil) to form a first dispersion, wherein the second liquid is immiscible with the first solution; (3) evaporating the first liquid from the first dispersion to precipitate the conjugate from the first dispersion; and (4) isolating the precipitate conjugate from the first dispersion. In the stirring step, the first solution can be added to the second liquid as small droplets.

The above method can further include the step of rinsing the isolated conjugate with a third liquid (e.g., hexane, heptane, or octane) which is miscible with the second liquid and not a solvent for the isolated conjugate. If desired, the isolated conjugate can be mixed with an aqueous mannitol solution prior to vacuum drying.

The biodegradable polymer in the above-described conjugate may contain at least one free carboxyl group (e.g., two to ten free carboxyl groups per polymer chain). Examples of carboxylic acid containing biodegradable polymers include polyesters containing units of lactic acid, e-caprolic acid, p-dioxanone, e-caprionic acid, substituted and unsubstituted trimethylene carbonate, 1,5-dioxepan-2-one, 1,4-dioxepan-2-one, glycolic acid, alkylene oxylate, cycloalkylene, cycloalkylene oxylate, alkylene succinate, or 3-hydroxy butyrate in optically active forms or as racemates; or copolymers of any of the above. Additional free carboxylic acid groups can be incorporated into the biodegradable polyester by reaction, e.g., ring opening polymerization or polycondensation, with polycarboxylic acids such as malic acid, tartaric acid, pamoic acid, citric acid, succinic anhydride, and glutaric anhydride. Thus, the biodegradable polymer can be a water insoluble polyester including lactic acid units with or without glycolic acid units. Other biodegradable polymers such as polyorthoesters, polyorthocarbonates, and polyantals may also be used. The biodegradable polymer may have an average degree of polymerization, e.g., average number of monomers per polymer chain, between 10 and 300.

The drug has one or more (e.g., one to ten) free amine groups. In one embodiment, the drug is an acid-stable peptide. Examples of suitable acid-stable peptides include growth hormone releasing peptide (GHRP), luteinizing hormone-releasing hormone (LHRH), adrenomedullin, growth hormone, somatostatin, bombesin, gastrin releasing peptide (GRP), calcitonin, bradykinin, galanin, melanocyte stimulating hormone (MSH), growth hormone releasing factor (GRF), amylin, adrenomedullin, tachykinins, secretin, parathyroid hormone (PTH), erkephalin, endothelin, calcitonin gene releasing peptide (CGRP), neuromedins, parathyroid hormone related protein (PTHrP), glucagon, neurotensin, adrenocorticotrophic hormone (ACTH), peptide YY (PYY), glucagon releasing peptide (GLP), vasoactive intestinal peptide (VIP), pituitary adenylated cyclase activating peptide (PACAP), motilin, substance P, neuropeptide Y (NPY), TSH, and analogs and fragments thereof. The drug may be soluble (e.g., greater than 0.1 mg/ml; preferably, greater than 1.0 mg/ml) in the first liquid.

Other features and advantages of the present invention will be apparent from the detailed description and from the claims.

It is believed that one skilled in the art can, based on the description herein, utilize the present invention to its fullest extent. The following specific embodiments are, therefore, to be construed as merely illustrative, and not limitative of the remainder of the disclosure in any way whatsoever.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

BEST MODES FOR CARRYING OUT THE INVENTION

EXAMPLE 1

18.0 g of a 6,000 g/mol 66/32/2 poly-L-lactic-co-glycolic-co-D,L-malic acid copolymer (66 percent L-lactic acid, 32 percent glycolic, and 2 percent malic acid; acid number of 0.373 milliequivalents/g) was dissolved in 180 g of acetone (solution of 10% copolymer by weight). 14.4 ml of 0.5 N aqueous NaOH was added to form the sodium carboxylate of the polymer. 4.28 g of the acetate salt of the peptide Lanreotide™ (Kinerton, Dublin, Ireland; D-Nal-c[Cys-Tyr-D-Trp-Val-Cys]-Thr-$NH_2$; acetate content=9.60 percent by weight) was separately dissolved in a mixture of 10 g of acetone and 10 g of deionized water. The amount of peptide dissolved corresponded to the stoichiometric ratio of acid groups from the copolymer (e.g., one) and the free amino groups for the peptide (e.g., two). The peptide solution was then added dropwise to the copolymer solution, and the resulting solution was stirred for two hours to allow for salt exchange and the resulting formation of the polymer/peptide ionic conjugate (PPIC).

EXAMPLE 2

In a temperature controlled jacketed reactor (Schott Glass AGB, Dublin, Ireland), a two liter bath of deionized water was precooled to 0° C. and was vigorously stirred. The above PPIC solution of Example 1 was then slowly added to the reactor using a Masterflex pump (Bioblock Scientific, Illkvch, France) which produced a flow rate of 10–15 ml/min through a silicone tubing fitted with a 19 gauge needle at its tip. The PPIC solution was fed through the needle that was positioned above a water bath at 0° C. The PPIC precipitated in the bath as small, solid particles. The solid particles were then separated from the supernatant by centrifugation (30 minutes at 5000 rpm and 0–5° C.), rinsed with fresh deionized water, resuspended water, recentrifuged, and then lyophilized. The isolated conjugate was filtered through a 100 μm sieve to remove any large particles which would not be capable of being injected through a 21 gauge needle. An analysis of the resulting particle sizes is described in Table 1.

EXAMPLE 3

The PPIC solution of Example 1 was also precipitated as described above in Example 2, except that a bath of ethanol at a temperature of −20° C. was used instead of a bath of water at 0° C. An analysis of the resulting particle sizes is described in Table I.

EXAMPLE 4

The PPIC solution of Example 1 was also dispersed at a controlled flow rate of 4 ml/min through an atomizing nozzle containing a hollow tip (Bioblock; 50 Watts, 20 kHz) over a bath of ethanol at −10° C. in a temperature controlled jacket reactor. In this nebulization process, the copolymer solution was released from the probe as a fine mist of small droplets. The small droplets fell into the ethanol bath, causing the deionized water and acetone to be extracted from the droplets. As a result, the copolymer droplets hardened as small, solid particles. The particles were then recovered by centrifugation and lyophilized. An analysis of the resulting particle sizes is listed in Table I. What is meant by Diameter −10 (i.e., D0.1), Diameter −50 (i.e., D0.5), or Diameter −90 (i.e., D0.9) is the smallest diameter which is greater than 10%, 50%, and 90% of the total particles, respectively. What is meant by specific area is the average specific area of the resulting particles.

TABLE I

| Example | Diameter-10 (μm) | Diameter-50 (μm) | Diameter-90 (μm) | Specific Area (m²/g) |
|---|---|---|---|---|
| 2 | 10 | 30 | 62 | 18.64 |
| 3 | 9 | 37 | 89 | 6.42 |
| 4 | 13 | 46 | 95 | 22.61 |

EXAMPLE 5

5.0 g of the PPIC described above in Example 4 was dissolved in 20 g of acetone (concentration of 20% PPIC by weight). This solution was then nebulized at a flow rate of 4.0 ml/min over 500 ml of bath of ethanol at −10° C. as described in Example 4. After preparation of the PPIC particles in the bath, 500 ml of deionized water was added to the bath, and the bath was then brought up to 0° C. The bath was then stirred for 30 min, brought up to 20° C., and stirred for an additional 30 min. The PPIC particles were then recovered by filtration and dried under vacuum at room temperature. An analysis of the resulting particles is listed in Table II.

TABLE II

| Example | D 0.1 (μm) | D 0.5 (μm) | D 0.9 (μm) | Specific Area (m²/g) |
|---|---|---|---|---|
| #4 | 13 | 46 | 95 | 22.61 |
| #5 | 50 | 99 | 180 | 0.11 |

As shown in Table II, different morphologies of particles were obtained. The particles of Example 4 were larger and had a lower specific area. As indicated by electron scanning microscope, the particles obtained in Example 4 were also more porous, likely because of the frozen water which remained in the particles upon precipitation. When the bath dispersion was returned to room temperature, the water thawed and flowed into the ethanol bath, leaving open channels in the microparticles. Consequently, these particles were more brittle and generated fragments of small size.

EXAMPLE 6

A solution of PPIC described above in Example 5 was nebulized at 2.5 ml/min over 1.5 liters of deionized water at 0° C. An analysis of the resulting particle sizes is listed in Table III.

EXAMPLE 7

A solution of PPIC described above in Example 5 was nebulized at 2.5 ml/min over 1.5 liters of ethanol at −10° C. An analysis of the resulting particle sizes is listed in Table III.

TABLE III

| Example | D 0.1 (μm) | D 0.5 (μm) | D 0.9 (μm) | Specific Area (m²/g) |
|---|---|---|---|---|
| 6 | 53.4 | 154.3 | 329.1 | n/a |
| 7 | 42.4 | 87.2 | 170.1 | 0.20 |

EXAMPLE 8

Two solutions of PPIC are prepared in acetone as described above in Example 5. The first solution has a PPIC concentration of 15% while the second solution has a PPIC concentration of 20%. The solutions are nebulized over a bath of ethanol at −10° C. at flow rates of 2.5, 3.5, and 5.0 ml/min as described in Example 5. An analysis of the resulting particle size is listed in Table IV.

TABLE IV

| Concentration | Feeding Rate (ml/min) | D 0.1 (μm) | D 0.5 (μm) | D 0.9 (μm) | Specific Area (m²/g) |
|---|---|---|---|---|---|
| 15% | 2.5 | 35.9 | 81.6 | 191.1 | 4.455 |
| 15% | 3.5 | 34.4 | 80.2 | 188.3 | 8.336 |
| 15% | 5.0 | 49.4 | 163.6 | 397.8 | n/a |
| 20% | 2.5 | 33.3 | 73.8 | 145.6 | 0.199 |
| 20% | 3.5 | 50.8 | 112.7 | 241.9 | 0.579 |
| 20% | 5.0 | 108.3 | 219.1 | 395.9 | n/a |

Analysis of the particles using scanning electron microscope revealed that the particle size and the specific area increased with the increase in feeding rate.

EXAMPLE 9

5.0 g of PPIC microparticles of Example 4 was dissolved in 45 g of acetone (concentration 10% by weight). The solution was then added dropwise over a vigorously stirred 500 ml n-hexane at room temperature. The n-hexane solution turned cloudy as particles of PPIC precipitated. The PPIC was removed by filtration and dried under vacuum at room temperature.

EXAMPLE 10

In a jacketed reactor, 3.0 g of the PPIC microparticles described in Example 2 was dispersed in a vigorously stirred 250 ml of 12,500 cs medical grade silicon oil (Dow Corning, Midland, Mich.) (of 1% PPIC by weight). After the stirring, the mixture was then heated to 120° C., which is above the Tg of 55° C. for the PPIC, and kept at this temperature for 30 minutes. During this heating, the isolated individual particles melted to fond spherical droplets. The dispersion was then cooled to 20° C. and then diluted with 1250 ml of hexane. The microspheres subsequently hardened, were recovered by filtration, were rinsed with fresh hexane, and were finally dried under vacuum. The characteristics of the obtained microspheres are reported in Table V. The final microspheres had a small diameter as compared to those of Example 2 as a result of the compaction of the particles during melting.

TABLE V

| Example | D 0.1 (µm) | D 0.5 (µm) | D 0.9 (µm) | Specific Area (m²/g) |
|---|---|---|---|---|
| #2 | 10 | 30 | 62 | 18.64 |
| #7 | 2 | 10 | 47 | <0.33 |

EXAMPLE 11

0.2 g of the PPIC microparticles described in Example 2 were dispersed in 5 ml of deionized water and vigorously stirred with a vortex shaker. 100 ml microliters of dichloromethane (DCM) was then added over the stirred dispersion. The addition of a small amount of DCM caused a swelling of the surface of the PPIC particles. Stirring was kept at room temperature for 4 hours, allowing for evaporation of DCM and consequential hardening of the swollen surface of the particles. A scanning electron microscope showed that the resulting particles were of spherical shape with a smoother surface as compared to the starting material. Both the particle size distribution was narrowed, and the maximum particle size was reduced as a result of the increase in the density of the particles.

EXAMPLE 12

One liter of sesame seed oil (Vitamins, Inc., Chicago, Ill.) was placed in a 2 liter, three necked flask immersed in a water bath. The oil was stirred at 600 rpm using a teflon stirring paddle connected to an overhead stirring motor. 500 mg of the surfactant, soybean lecithin, (Sigma Chemicals, St. Louis, Mo.) was added to the sesame seed oil, and the mixture was stirred for 10 min. 10 g of a PPIC formulation was then dissolved in 100 ml acetonitrile to give a clear solution. The PPIC compositions were made using Lanreotide™ conjugated with one of the following three polymers: 64/34/2 poly-DL-lactic-co-glycolic-D,L-malic acid copolymer (M.W. avg 6,000) (Composition 1); 74/24/2 poly-DL-lactic-co-glycolic-D,L-malic acid copolymer (M.W. avg 6,000) (Composition 2); and 98/2 poly-DL-lactic-co-D,L-malic acid copolymer (Composition 3).

This clear PPIC solution was added dropwise through a dropping funnel. When the addition was completed, the temperature of the external water bath was raised to 40° C., and the oil was left stirring for 20 h. One liter of hexane was then added to dilute the sesame seed oil, and the oil was filtered through a medium fritted funnel. The microspheres collected in the filter funnel were further washed several times with 500 ml in total volume of hexane. The particles are dried at 36° C. for two days under vacuum. Characteristics of the resulting microspheres are presented in Table VI.

TABLE VI

| Composition | D 0.1 (µm) | D 0.5 (µm) | D 0.9 (µm) | Specific Area (m²/g) |
|---|---|---|---|---|
| 1 | 13 | 28 | 57 | 0.1426 |
| 2 | 13 | 25 | 59 | 0.1395 |
| 3 | 14 | 25 | 51 | 0.1480 |

EXAMPLE 13

Reactor was loaded with monomers glycolide (Purac Biochem, Netherlands, 84.83 g), lactide (PuracBiochem, Netherlands, 210.67 g) and L(+)-tartaric acid (Riedel-de Haen, Seelze, Germany, article number 33,801, 4.50 g) and stannous 2-ethyl hexanoate (Sigma, St. Louis, Mo., USA, article number S-3252) in toluene (Riedel-de Haen, Seelze, Germany) solution (0.1025 M, 4.34 ml). The L(+)-tartaric acid was previously dried over phosphorous pentoxide (Riedel-de Haen, Seelze, Germany) in an Abderhalden drying apparatus for 10 hours. The reactor (connected to pump via a liquid nitrogen trap) was then put under vacuum (0.04 mbar) with stirring for 50 minutes to remove toluene. The reactor, under an atmosphere of oxygen-free nitrogen (BOC gases, Dublin, Ireland, moisture content of 8 VPM), was then immersed in an oil bath (Temperature=200° C.) and stirring was increased to 125 rpm. Prior to immersion, a heating tape (Thermolyne type 45500, input control setting=4) was placed on the reactor lid. The time taken to completely melt the reactor contents was noted, typically 10 minutes for a load of 300 g at 200° C. Samples were taken every hour during synthesis and analyzed by GPC to determine the percentage residual monomer and to obtain values for average molecular weight by number (Mn) and by weight (Mw). Typical reaction times are of the order of 6 hours.

An amorphous copolymer was obtained comprising 66.21% lactide units, 33.11% glycolide units, and 0.68% tartaric acid units (66/33/1 PLGTA). The acid number of the titration was determined to 0.303 milliequivalents/g (meq/g; the normality of NaOH multiplied by the volume of NaOH solution required to neutralize one gram of polyester). The average number average molecular weight of the copolymer had a value of 10,250, the average weight molecular weight of the copolymer was 11,910 giving a Mw/Mn value of 1.16.

41.32 g of the above 10,000 g/mol 66/32/2 poly-L-lactic-co-glycolic-co-L( +)-tartaric acid copolymer (acid number=0.303 meq/g) was dissolved in 165.52 g of acetone (Riedel-de Haen, Seelze, Germany) by sonication in a Branson sonication bath (Branson, Danbury, Conn., USA) to give a solution with a concentration of 19.98% PLGTA by weight.

To this solution was added 37.6 ml 0.2 N sodium carbonate (Aldrich, Gillingham, Dorset, UK) thus providing a 1.2 times excess of sodium over copolymer carboxyl groups. The solution was left to stir for 30 minutes to aid sodium salt formation. It was then fed to an atomizer nozzle at 8.0 ml/min using a Masterflex pump (Cole Parmer, Barrington, Ill., USA). The solution was nebulized into a 6 L jacketed reactor containing 2 L of de-ionized water cooled to 2.5° C.

using a circulation bath (Huber, Offenburg, Germany). This water was stirred to 350 rpm using a 4-blade paddle linked to a stirrer motor.

Once nebulization was complete, the dispersion was placed in 6 centrifuge bottles and spun at 5000 rpm for 30 minutes in a Sorvall centrifuge (DuPont Sorvall Products, Wilmington. Del., USA). The resultant centrifuge cakes were resuspended in de-ionized water and re-spun. The supernatant was discarded and the cakes were frozen in a freezer overnight before being dried in a small-scale lyophilizer (Edwards, Crawley, West Sussex, UK) the next day. 33.16 g of washed copolymer were recovered representing a yield of 80.24%.

4.92 g of the above 10,000 g/mol 66/33/1 poly-L-lactic-co-glycolic-co-D,L-tartaric acid copolymer (66 percent L-lactic acid, 33 percent glycolic acid, and 1 percent tartaric acid) was dissolved in 11.58 g of acetonitrile (Ridel-de Haen, Seelze, Germany; HPLC grade) by sonication in a Branson sonication bath (Branson, Danbury, Conn., USA) and stirred on a stir-plate producing a solution with a concentration of 29.82% of PLGTA by weight.

This copolymer/acetonitrile solution was fed from a glass reservoir through an atomizer nozzle using an FMI revolving piston pump (FMI, Oyster Bay, N.Y., USA) set at 2.0 ml/min. The atomizer output power was set at 50 W with an amplitude of 80%. The solution was nebulized into a 6 L jacketed reactor containing 1.5 L of general purpose reagent isopropyl alcohol (Labscan, Dublin, Ireland), cooled to $-70°$ C. by solid $CO_2$ pellets (AIG, Dublin, Ireland), and stirred at 300 rpm with a 4-blade paddle linked to a stirrer motor. The temperature of the isopropyl alcohol remained at or close to $-70°$ C. throughout nebulization which lasted for approximately 8 minutes.

Once nebulization was complete, the dispersion was allowed to warm to 10° C. of its own accord over a period of 5.5 hours. It was then filtered over a Whatman No. 1 filter paper (9 cm diameter) with the aid of a vacuum. The filter paper and cake were placed in a desiccator along with silica gel drying chips and a vacuum was pulled through an automatic refrigeration trap at $-110°$ C. After 24 hours 4.24 g of material were recovered. An analysis of the resulting particles is listed in Table VII.

TABLE VII

| Example # | D 0.1 (μm) | D 0.5 (μm) | D 0.9 (μm) | Specific Area ($\mu^2/g$) |
|---|---|---|---|---|
| 13 | 31 | 68 | 139 | 0.16 |

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

The invention claimed is:

1. A biodegradable polymer wherein said polymer contains one or more members selected from the group consisting of lactic acid, ε-caproic acid, glycolic acid, trimethylene carbonate p-dioxanone tartanc acid and any optically active isomers, racemates or copolymers thereof provided that tartaric acid is a required member of said polymer.

2. The biodegradable polymer according to claim 1 consisting of lactic acid, glycolic acid and tartaric acid and any optically active isomers, racemates or copolymers thereof.

* * * * *